United States Patent [19]

Morita et al.

[11] Patent Number: 5,018,528
[45] Date of Patent: May 28, 1991

[54] PULSE DOPPLER ULTRASONIC DIAGNOSTIC SYSTEM

[75] Inventors: Dai Morita; Yuichi Hirota; Takao Higashiizumi, all of Tokyo, Japan

[73] Assignee: Yokogawa Medical Systems, Limited, Tokyo, Japan

[21] Appl. No.: 432,730

[22] PCT Filed: Apr. 30, 1988

[86] PCT No.: PCT/JP88/00441
§ 371 Date: Oct. 23, 1989
§ 102(e) Date: Oct. 23, 1989

[87] PCT Pub. No.: WO88/08278
PCT Pub. Date: Nov. 3, 1988

[30] Foreign Application Priority Data

Apr. 30, 1987 [JP] Japan ................................ 62-107064

[51] Int. Cl.$^5$ ............................................. A61B 8/06
[52] U.S. Cl. ............................. 128/661.09; 73/861.25
[58] Field of Search ..................... 128/661.07-661.10; 73/861.25

[56] References Cited

U.S. PATENT DOCUMENTS 4,819,652  4/1989  Micco ........................... 128/661.09
4,848,356  7/1989  Nakamura et al. .

Primary Examiner—Francis Jaworski
Attorney, Agent, or Firm—Moonray Kojima

[57] ABSTRACT

A pulse Doppler ultrasonic diagnostic system capable of invariably obtaining best Doppler signals with respect to an arbitrary sample volume length under the condition that mean power of transmit ultrasonic waves is restricted to a constant value. The system has a device for making the mean power constant and a device for making a burst wave number variable for transmit ultrasonic signals and also includes a device for making an integration interval length variable for ultrasonic receiving signals, thereby controlling the burst wave number of the transmit ultrasonic waves and the integration interval length of the ultrasonic receiving signals.

1 Claim, 2 Drawing Sheets

PULSE DOPPLER ULTRASONIC DIAGNOSTIC SYSTEM

BACKGROUND OF THE INVENTION

1. Field of the Invention

The present invention relates to an improvement of a pulse Doppler ultrasonic diagnostic system.

2. Description of the Prior Art

A pulse Doppler ultrasonic diagnostic system is intended to obtain a kinetic direction and a velocity of a ultrasonic scatterer by extracting only ultrasonic scattering signals from a region of concern within a subject for examination by processing Doppler shift components. In order to fetch the ultrasonic signals from the region, signals from an interval $\Delta x$ between a depth $x$ and a depth $x + \Delta x$ have to be accumulated in any form and sample-held. The accumulation of signals involves the use of a method of integrating reflection signals with transmit ultrasonic waves serving as single pulse waves for a period equivalent to a sample volume length $\Delta y$ by use of an interval integrator, or alternatively a method of sample-holding the reflection signal with the transmit ultrasonic waves serving as burst waves, the number of waves corresponds to the interval $\Delta$ after a given time has passed, with a wave transmitting time being defined as an origin. Mean power of the transmit ultrasonic waves is limited to a constant value or under in terms of security in connection with influences of the ultrasonic waves on a human body. Under such a condition that the mean power is restricted to the constant value, however, it is impossible to invariably obtain best Doppler signals with respect to an arbitrary sample volume length simply by employing any one of the above-mentioned methods.

SUMMARY OF THE INVENTION

It is a primary object of the present invention to provide a pulse Doppler ultrasonic diagnostic system capable of obtaining the best Doppler signals with respect to an arbitrary sample volume length under a condition that mean power of transmit ultrasonic waves is limited to a constant value.

To accomplish this object, according to one aspect of the invention, there is provided a pulse Doppler ultrasonic diagnostic system comprising: a means for making mean power constant in connection with transmit ultrasonic signals; a means for making the number of burst waves variable; and a means for making an integration interval variable in connection with ultrasonic receiving signals, characterized in that best Doppler signals are obtained by controlling both the number of burst waves of the transmit ultrasonic waves and the integration interval of the ultrasonic receiving signals.

BRIEF DESCRIPTION OF THE DRAWINGS

Other objects and advantages of the present invention will become apparent during the following discussion taken in conjunction with the accompanying drawings, in which.

DESCRIPTION OF THE PREFERRED EMBODIMENT

Figure 1:
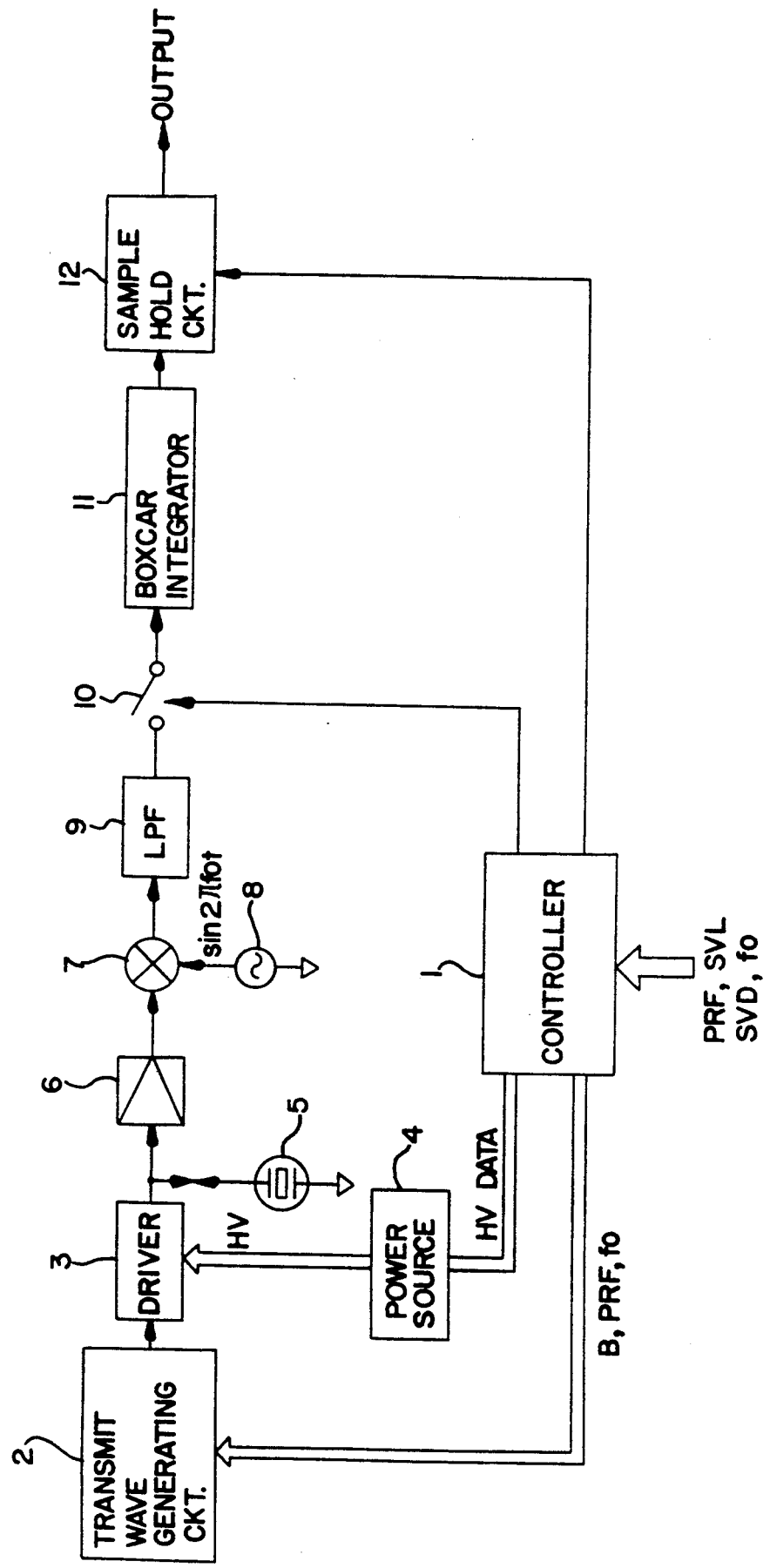
FIG. 1 is a block diagram depicting a conceptual construction of one embodiment of the present invention.

An illustrative embodiment of the present invention will hereinafter be described in detail with reference to the accompanying drawings. Referring first to FIG. 1, the numeral 1 represents a controller for outputting control signals corresponding to a pulse repeating frequency (hereinafter abbreviated to PRF), a sample volume depth (SVD), a sample volume length (SVL) and a transmit central frequency (fo) which are set from outside. Designated at 2 is a transmit wave generating circuit for generating high frequency signals upon receiving the control signals relative to the number of burst waves, a PRF and a transmit central frequency from the controller 1, and further outputting the generated high frequency signals to a driver 3. The driver 3 in turn outputs the high frequency signals by power-amplifying them after receiving voltages (hereinafter referred to as HV) from a transmit power source 4. The transmit power source 4 functions to supply the driver 3 with the voltages HV determined on the basis of HV data defined as control signals of the controller 1. The high frequency signals of the outputs of the driver 3 are inputted as driving signals to a vibrator element 5 and transmitted to the subject for examination after being converted into ultrasonic signals. Signals reflected by a ultrasonic scatterer of the subject are received by the vibrator element and then amplified by a preamplifier 6. The receiving signals amplified by the preamplifier 6 are mixed with output signals of $\sin 2\pi fo$ from a local oscillator 8 by means of a mixer 7 and are then detected. High frequency components of the detected signals are eliminated by means of a low-pass filter (LPF) 9. Note that only one vibrator element 5 is depicted for simplifying the explanation, but normally a plurality of elements are arrayed. A plurality of output signals of the driver 3 are supplied via a well-known adequate transmit beam forming means (not illustrated) to the plurality of elements. The receiving signals of the plurality of vibrator elements are amplified and detected separately by use of the preamplifiers 6 and the mixers 7 which are provided to constitute a plurality of systems, correspondingly. Subsequently, the receiving signals are synthesized through the known adequate reception beam forming means (not illustrated). The output signals of the LPF 9 are inputted to a range gate 10. The range gate 10 in turn extracts Doppler signals in a depth set by the controller 1 under control of range gate control pulses given from the controller 1 which determine a sample volume depth and an integration interval length. The numeral 11 denotes a boxcar integrator for integrating the Doppler signals on a time-axis for a given period which are extracted by the range gate 10. Indicated at 12 is a sample hold circuit for holding output data of the boxcar integrator with sample hold control pulses given from the controller 1. Circuits subsequent to the sample hold circuit 12 are provided with Doppler signal analyzing means (not illustrated) which employ FFTs and are common to a known ordinary pulse Doppler device.

The description will next be focused on operations of the thus constructed system. An operator of this system sets a PRF and a central frequency fo of ultrasonic waves for transmission in the controller 1. There are also set a sample volume depth SVD and a sample volume length SVL within the subject from which the Doppler signals are to be taken. The controller 1 computes a burst wave number B of optimal transmit signals under such a condition that the ultrasonic mean power is constant, a driver power source voltage HV for keeping the ultrasonic mean power at a constant value and an optimal integration interval length R under the condition that the ultrasonic mean power is kept constant on the basis of the set data by a method which will hereinafter be described in greater detail. Based on the set value and the computed results, the controller 1 supplies data on the PRF and on the burst wave number B to the transmit wave generating circuit 2, wherein high frequency signals based on such data are generated. Then, HV data are imparted to the transmit power source 4, thereby generating the HV based on the data as power source voltages for the driver 3. The driver 3 in turn outputs both the high frequency signals given from the transmit wave generating circuit 2 and high frequency driving signals determined by the power source voltages given from the transmit power source 4, thereby transmitting ultrasonic pulse signals from the vibrator elements 5. Ultrasonic echo signals reflected and returned from within the subject are received by the vibrator elements 5 preparatory for conversion into electric signals. Subsequently, the ultrasonic echo signals are mixed with frequency signals $\sin 2\pi fo$ of the local oscillator 8 by means of the mixer 7 and then detected after being amplified by the preamplifier 6. Unnecessary high frequency components of low frequency signals obtained by such detection are removed by the low-pass filter 9 and inputted to the range gate 10. The range gate 10 receives range gate control pulses based on the calculated value of the integration interval length R at a timing corresponding to the sample volume depth and then inputs to the boxcar integrator 11 the Doppler signals after taking in these signals existing in the interval length R. The boxcar integrator 11 integrates the signals of the integration interval R which have passed the range gate 10. Output signals of the boxcar integrator 11 are held by the sample hold circuit 12 in conformity with the control signals of the controller 1. Integrated outputs of the boxcar integrator 11 are cleared after being held by the sample hold circuit 12.

When giving the central frequency fo, the sample volume depth SVD, the sample volume length SVL and the pulse repeating frequency PRF, there is effected, in the following manner, a calculation for obtaining an integration interval length R and an optimal burst wave number B under the condition that the ultrasonic mean power is constant. Let $\tau$ be a pulse width of the ultrasonic wave, let R be an integration interval and let L a sample volume length. An equation between these three elements will be expressed such as:

$$2L/c = R + \tau \quad (1)$$

where c; acoustic velocity

On the other hand, when cutting off a certain part of a flow of blood which presents a constant flow velocity, scattering signal power Ps from the blood is expressed such as:

$$Ps = k.Pi.W.c.\tau(\tau/T).N.\sigma.\exp\{-22/\alpha fo^n x\}/x^2 \quad (2)$$

where k; coefficient
Pi; irradiation ultrasonic power
W; ultrasonic beam width
T; pulse repeating cycle (1/PRF)
N; the number of corpuscles per unit volume
$\sigma$; scattering sectional area of one corpuscle
$\alpha$; attenuation constant
fo; central frequency
n; positive real number which differs depending on media and indicates frequency dependency of attenuation characteristics.

Supposing that the ultrasonic beam width W, the attenuation constant $\alpha$ and the scattering sectional area $\sigma$ of one corpuscle do not convert even when the burst wave number B varies, the formula (2) can be expressed as follows:

$$Ps = K.\tau.(Pi.\tau/T) \quad (3)$$

where K is the coefficient.

Ps is the mean power. Taking into consideration the fact that cutting and sample holding processes thereof are effected by the range gate 10 in the Doppler signal processing unit, an input amplitude D of the boxcar integrator 11 interposed between the range gate 10 and the sample hold circuit 12 is given by:

$$D = K'\{\tau.Pi.\tau/T\}^{1/8} \quad (4)$$

Supposing that a phase of scattering waves from the corpuscles is fixed while the range gate 10 is open, an amplitude E of the outputs of the boxcar integrator 11 is expressed such as:

$$E = K''.R.\{\tau.(Pi.\tau/T)\}^{1/8} \quad (5)$$

Eliminating R from the formulae (1) and (5), the following equation will be established.

$$E = K''.\{(2L/c) - \tau\}.\{\tau.(Pi.\tau/T)\}^{\frac{1}{2}} \quad (6)$$

Thus obtained E is a quantity proportional to a Doppler spectrum amplitude.

Next, for the purpose of obtaining the burst wave number B optimal to L of a certain value, there is obtained a ratio $G_{(B)}$ of a Doppler output $B_{(1)}$ when B=1 to a Doppler output $B_{(B)}$ when B takes a variety of large values in the following manner.

$$\begin{aligned} G_{(B)} &= B_{(B)}/B_{(1)} \\ &= [\{2L/c - \tau_{(B)}\}/\{2L/c - \tau_{(1)}\}] \cdot [\{\tau_{(B)} \cdot Pi_{(B)} \cdot \tau_{(B)}/T\}/ \\ &\quad \{\tau_{(1)} \cdot Pi_{(1)} \cdot \tau_{(1)}/T\}]^{\frac{1}{2}} \end{aligned} \quad (7)$$

where $\tau(B)$; pulse width when the burst wave number is B
$\tau(1)$; pulse width when the burst wave number is 1
$Pi_{(B)}$; irradiation ultrasonic power when the burst wave number is B
$Pi_{(1)}$; irradiation ultrasonic power when the burst wave number is 1

If the ultrasonic mean power is controlled to a constant value in conformity with a safety standard, the ultrasonic power is invariably equal to a numeric value obtained by dividing a product of the pulse width by the repeating cycle, i.e., the ultrasonic power is always equal to a product associated with a duty cycle irrespective of the burst wave number B. Hence, $$Pi_{(B)} \cdot \tau_{(B)}/T = Pi(1) \cdot \tau_{(1)}/T$$

$(B) = B/fo$, and hence the formula (7) can be simplified into a formula (8).

$$G_{(B)} = \{(2L/c - B/fo) / (2L/c - 1/fo)\} \cdot B^{\frac{1}{2}} \quad (8)$$

Figure 2:
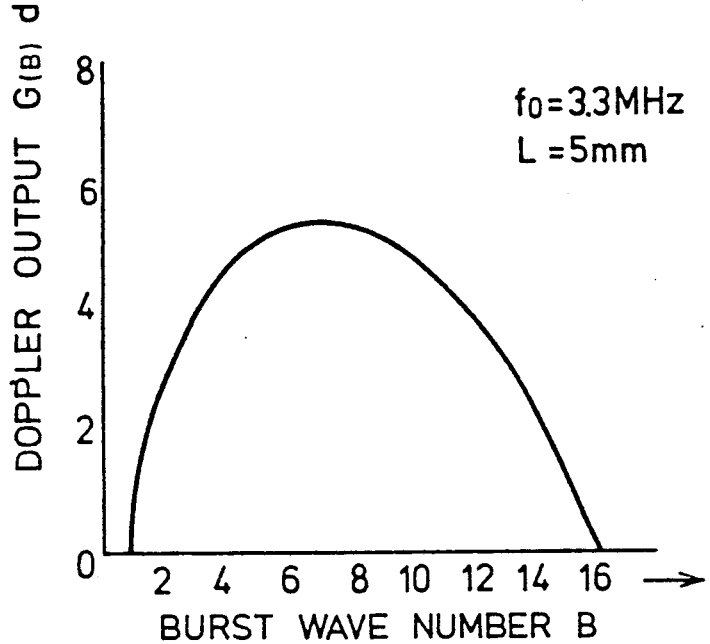
FIG. 2 is a graph showing variations in Doppler outputs versus the number of burst waves when setting constant a wave transmit central frequency and a sample volume length.

FIG. 2 shows arithmetic results of the Doppler outputs for every burst wave number B by using the formula (8) when fo = 3.3 MHz and L = 5 mm. FIG. 2 shows a curve, where the axis of abscissa indicates the burst wave number B, and the axis of ordinate indicates $G_{(B)}$ graduated with dB. It can be observed from the graph in FIG. 2 that a condition for the maximum Doppler output for L of a certain value is given by $dG_{(B)}/dB = 0$.

If $2L/c = \alpha$, $$dG_{(B)}/dB = (-1/fo) B^{\frac{1}{2}} + (\tfrac{1}{2})(\alpha - B/fo) B^{-\frac{1}{2}}$$

$$\alpha - (B/fo) = 2B/fo$$

$$3B/fo = \alpha = 2L/c$$

$$\therefore B = (\tfrac{2}{3})(L/c) \cdot fo \quad (9)$$

From the formulae (1) and (9) as well as from $G_{(B)} = B/fo$, the integration interval length R at this time is given by:

$$R = (4/3) L/c \quad (10)$$

Figure 3:
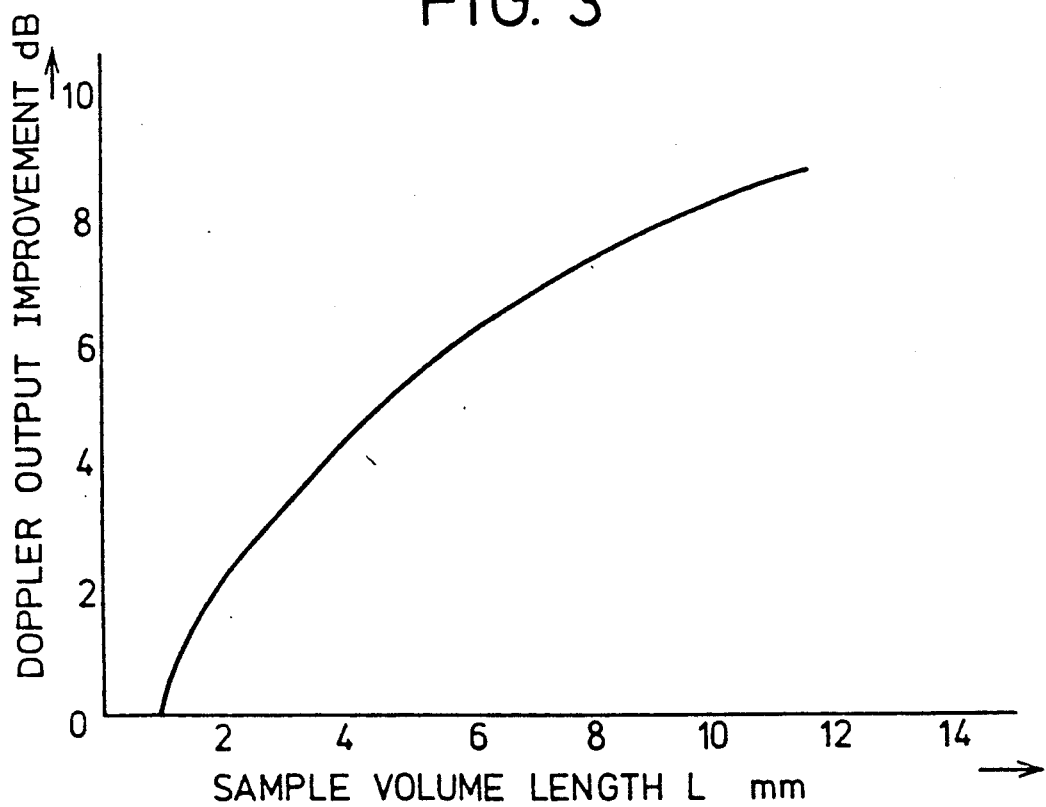
FIG. 3 is a graph showing variations in degree of improvement of the Doppler outputs with respect to the sample volume length when controlling the number of burst waves and a time integration interval length.

As is obvious from the foregoing arithmetic, when the burst wave number B and the integration interval length R satisfy the formulae (9) and (10), the maximum Doppler output can be obtained. When controlling the burst wave number B and the integration interval length R in accordance with the formulae (9) and (10), FIG. 3 shows a degree of improvement of the Doppler output in the case of B = 1 with respect to values of the sample volume length L.

Although the preferred embodiment of the present invention has been described in detail, a variety of modifications can be effected with facility by one skilled in the art to which the invention belongs without departing from the scope of the following claims.

What is claimed is:

1. In a pulse Doppler ultrasonic diagnostic system comprising generating means, vibrator means, range gate means, and integrator means, the improvement comprising control means for receiving information representative of a volume to be sampled and for generating a first control signal representing a selected optimum burst wave number and a second control signal representing a selected integration interval in response to said received information said generating means, under the control of said first control signal, for generating ultrasonic waves of a substantially constant mean power and of said selected wave burst number, for application to said vibration means; and said range gate means, under the control of said second control signal, for applying to said integrator means during said selected integration interval signals received from said vibrator means;

whereby optimal Doppler signals are obtained for a selected sample volume.

* * * * *